(12) United States Patent
Gebauer et al.

(10) Patent No.: US 10,589,239 B2
(45) Date of Patent: Mar. 17, 2020

(54) FLUID MIXING IN A DISPOSABLE FLUID PROCESSING SYSTEM

(75) Inventors: Klaus Gebauer, Uppsala (SE); Patric Fricking, Uppsala (SE); Bjorn Jaderlund, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 217 days.

(21) Appl. No.: 13/808,606

(22) PCT Filed: Jun. 27, 2011

(86) PCT No.: PCT/SE2011/050850
§ 371 (c)(1),
(2), (4) Date: Jan. 7, 2013

(87) PCT Pub. No.: WO2012/005663
PCT Pub. Date: Jan. 12, 2012

(65) Prior Publication Data
US 2013/0112624 A1    May 9, 2013

(30) Foreign Application Priority Data
Jul. 7, 2010   (SE) ..................... 1050743

(51) Int. Cl.
*B01F 15/02*  (2006.01)
*G05D 11/13*  (2006.01)
(Continued)

(52) U.S. Cl.
CPC .......... *B01F 15/0216* (2013.01); *B01D 15/12* (2013.01); *B01D 15/163* (2013.01);
(Continued)

(58) Field of Classification Search
None
See application file for complete search history.

(56) References Cited

U.S. PATENT DOCUMENTS

| 4,239,623 A | 12/1980 | Schrenker |
| 4,772,388 A | 9/1988 | Allington |

(Continued)

FOREIGN PATENT DOCUMENTS

| EP | 1777515 B1 | 5/2009 |
| WO | WO 2001/052009 | 7/2001 |

(Continued)

OTHER PUBLICATIONS

"Pump". Dictionary.com definition. Accessed on Aug. 4, 2015 from http://dictionary.reference.com/browse/pump.*

(Continued)

*Primary Examiner* — Kara M Peo
(74) *Attorney, Agent, or Firm* — Eversheds Sutherland (US) LLP

(57) ABSTRACT

High accuracy mixing of fluids in a disposable fluid processing system with at least two pumps is provided by a method where a calibration fluid volume is pumped through each pump via a flow meter at at least one calibration pump speed while registering the flow rate using data output from the flow meter, a pump calibration function is calculated from the calibration pump speed and flow rate data and two or more operation fluids are mixed to a predetermined mixture ratio and predetermined flow rate by controlling the pump speed of the respective pumps in accordance with the pump calibration functions.

10 Claims, 2 Drawing Sheets

(51) Int. Cl.
    *G01N 30/34*     (2006.01)
    *B01D 15/16*     (2006.01)
    *B01D 15/12*     (2006.01)
    *G01N 30/86*     (2006.01)

(52) U.S. Cl.
    CPC ........... *B01D 15/166* (2013.01); *G01N 30/34* (2013.01); *G05D 11/132* (2013.01); *G01N 30/8658* (2013.01); *G01N 30/8665* (2013.01); *G01N 2030/347* (2013.01)

(56) References Cited

U.S. PATENT DOCUMENTS

| | | | | |
|---|---|---|---|---|
| 5,037,649 | A * | 8/1991 | Balint et al. | 424/140.1 |
| 5,360,320 | A | 11/1994 | Jameson et al. | |
| 5,423,661 | A * | 6/1995 | Gabeler | F04C 14/08 210/101 |
| 6,942,804 | B2 * | 9/2005 | Herman | 210/657 |
| 7,299,944 | B2 * | 11/2007 | Roady | B67D 1/0006 222/1 |
| 2005/0109698 | A1 | 5/2005 | Gerhardt et al. | |
| 2007/0175511 | A1 | 8/2007 | Doerr et al. | |

FOREIGN PATENT DOCUMENTS

| | | |
|---|---|---|
| WO | 2005050190 | 6/2005 |
| WO | WO 2005/113457 | 12/2005 |

OTHER PUBLICATIONS

"Valve". Dictionary.com definition. Accessed on Aug. 4, 2015 from http://dictionary.reference.com/browse/valve.*

"Calibrate". Dictionary.com definition. Accessed on Aug. 4, 2015 from http://dictionary.reference.com/browse/calibrate.*

* cited by examiner

FLUID MIXING IN A DISPOSABLE FLUID PROCESSING SYSTEM

CROSS-REFERENCE TO RELATED APPLICATIONS

This application is a filing under 35 U.S.C. 371 of international application number PCT/SE2011/050850, filed Jun. 27, 2011, published on Jan. 12, 2012 as WO 2012/005663, which claims priority to application number 1050743-2 filed in Sweden on Jul. 7, 2010.

TECHNICAL FIELD OF THE INVENTION

The present invention relates to disposable fluid processing systems. More specifically it relates to calibration of pumps in connection with fluid mixing in disposable fluid processing systems.

BACKGROUND OF THE INVENTION

Production of biopharmaceuticals such as proteins, peptides, vaccines etc. involves several unit operations where mixtures of fluids (typically aqueous buffers) have to be prepared to high precision and accuracy. Examples of such unit operations are chromatography, where continuous gradients or step gradients are commonly used for elution of columns, buffer exchange, formulation and any operation where a buffer or other fluid is prepared by in-line dilution of a concentrate. For accurate mixing it is necessary to have good control of the flow rates of the fluids to be mixed. In traditional bioprocessing operations this has been achieved with positive displacement pumps (typically piston pumps) of high precision and accuracy, which are stable with time and can optionally be supplemented with feedback loops from accurate in-line flow meters, as described e.g. in US Pat Appl. 2007/0000308.

Due to the high regulatory demands on sanitation and validation of sanitation between batches and campaigns, there is today a strong trend towards bioprocessing plants where all wetted parts are disposable. This means that the sanitation and validation costs can be avoided, which is particularly important for smaller scale bioprocessing plants used e.g. to produce material for clinical trials.

In a set-up for disposable bioprocessing, it is preferred to use pumps where the wetted parts are only disposable tubing, e.g. in peristaltic pumps, or low-cost disposable pump heads, e.g. for specially designed membrane pumps or centrifugal pumps. Such pumps necessarily give lower accuracy and time stability than the traditional piston pumps, which necessitates calibration under the running conditions immediately before use. Peristaltic pumps are often preferred in disposable bioprocessing as they do not require disposable pump heads, but they are particularly prone to drift with time due to movement of the tubing during operation. For calibration, some type of flow meter is necessary and even the flow meter must have disposable wetted parts.

Such flow meters can be made to good precision, e.g. in the case of ultrasound flow meters as described in U.S. Pat. No. 7,673,527. Their accuracy is however limited as precalibration of the disposable flow meters is normally avoided to avoid potential contamination with a calibration fluid. This limitation in accuracy does not pose any major difficulties when only one buffer is to be supplied as e.g. in a one-pump chromatography system like similar to the AktaReady™ liquid chromatography system. In mixing systems, the demand for accurate composition control of the fluid mixture is however high, for example in gradient elution of chromatography columns where the separation selectivity depends strongly on the gradient composition.

There is thus a need for a method to provide accurate mixing of fluids in disposable systems using pumps and flow meters with low-cost disposable wetted parts.

SUMMARY OF THE INVENTION

One aspect of the invention is to provide high accuracy when mixing fluids in a disposable fluid processing system. This is achieved with a method for conveying a mixture of at least two operation fluids to a receptacle in a disposable fluid processing system, and the disposable fluid processing system including at least one flow meter and at least two pumps, each pump connected to at least one source of fluid.

One advantage with such a method is that only one disposable flow meter needs to be used and that a high accuracy in the composition of the mixture can be achieved despite a low accuracy of the flow meter.

Further suitable embodiments of the invention are described in the depending claims.

DEFINITIONS

The term "receptacle" herein means a vessel arranged for receiving a fluid or a mixture of fluids. Examples of receptacles include chromatography columns, filters, bioreactors, bags, tanks, bottles etc.

The term "linear character" herein means that the flow rate produced by a pump is an essentially linear function of the pump speed.

The term "disposable" herein means that a piece of equipment is only intended for short-term use, such as single use. The single use can be either in a single batch or in a single campaign of batches.

DETAILED DESCRIPTION OF EMBODIMENTS

Figure 1:
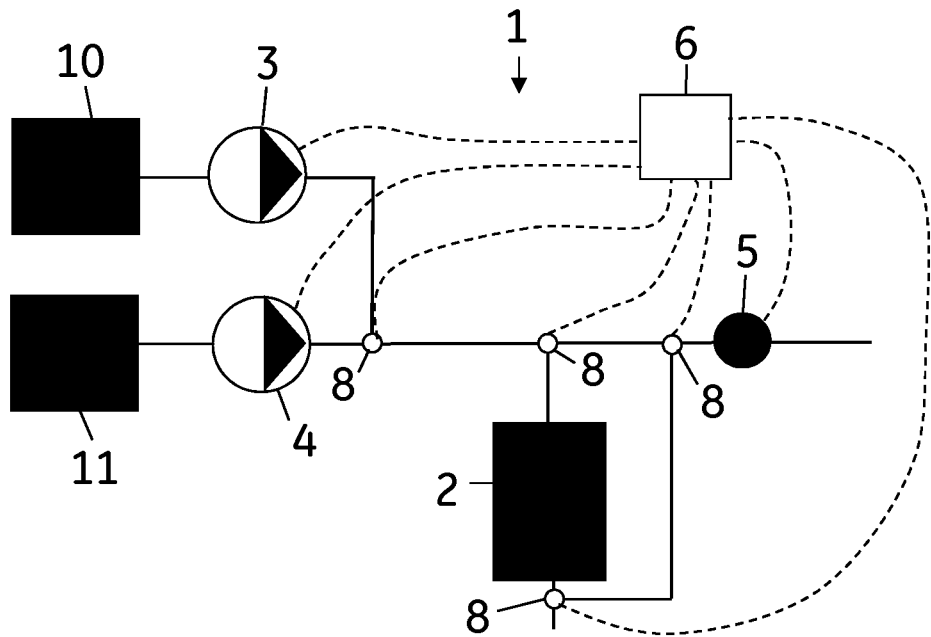
FIG. 1 shows a disposable fluid processing system according to the invention.
Figure 2:
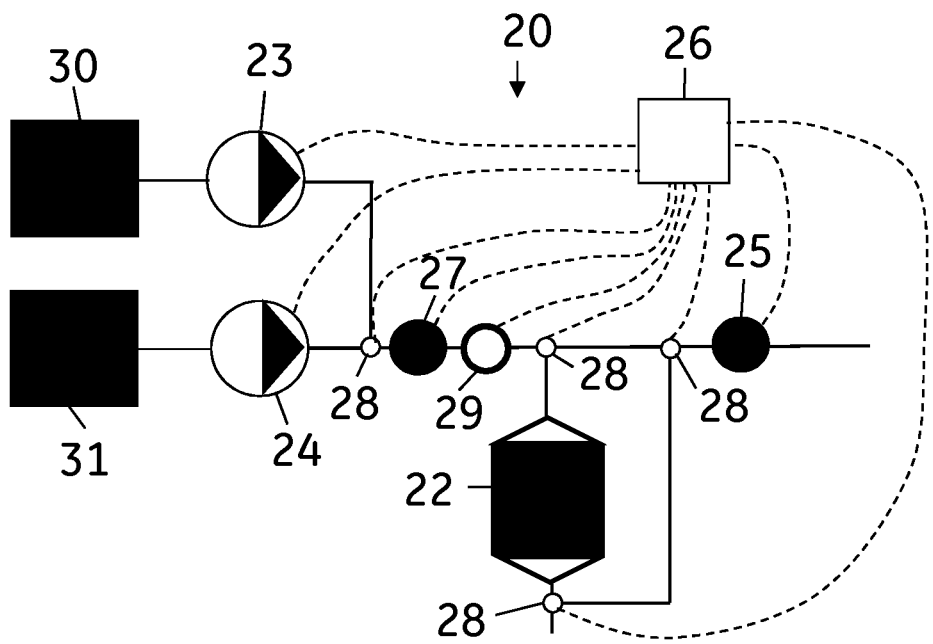
FIG. 2. shows a disposable fluid processing system with a throttle valve according to the invention.
Figure 3:
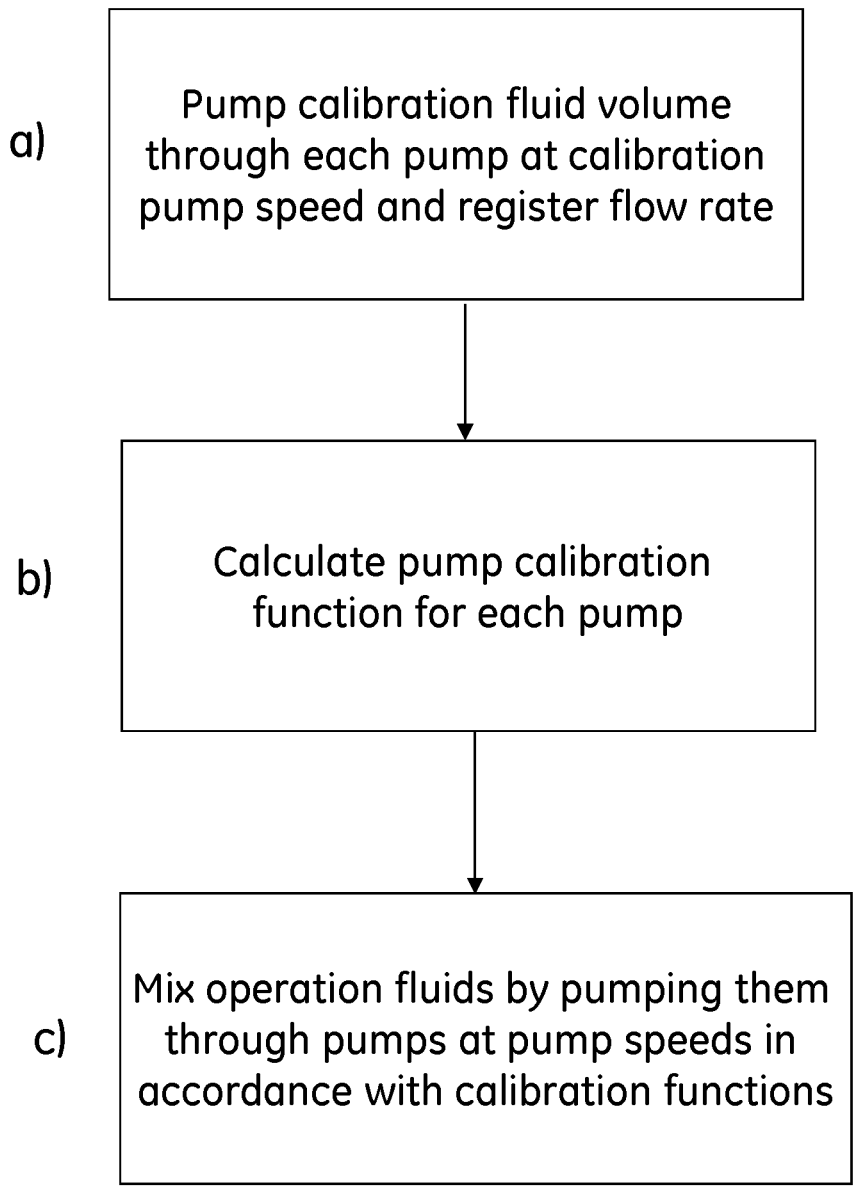
FIG. 3 shows a method for conveying a mixture of fluids according to the invention.

In one aspect illustrated by FIGS. 1-3, the present invention discloses a method for conveying a mixture of at least two operation fluids to a receptacle 2 and 22 (as depicted in FIG. 2) in a disposable fluid processing system 1 and 20 (as depicted in FIG. 2) such as e.g. a disposable chromatography system, a disposable filtration system, a disposable cell culture system or a disposable in-line dilution system. The disposable fluid processing system 1 and 20 comprises at least one flow meter 5 and 25 (as depicted in FIG. 2) and at least two pumps and 4; 23 and 24 (as depicted in FIG. 2), wherein each pump is connected to at least one source of fluid 10, 11, 30 and 31 (as depicted in FIG. 2).

The method comprises the steps of a) for each pump pumping a calibration fluid volume through the pump 3, 4, 23 and 24 to, from or via the flow meter 5 and 25 at at least one calibration pump speed and registering the flow rate using data output from the flow meter 5 and 25, b) for each pump calculating a pump calibration function from the calibration pump speed and the registered flow rate and c) mixing two or more operation fluids to a predetermined mixture ratio and predetermined flow rate by controlling the pump speed of the respective pumps 3, 4, 23 and 24 in accordance with the respective pump calibration functions.

By using a single flow meter in this way, the pumps will be well calibrated in relation to each other and a highly accurate composition of the mixture can be provided. Step a) can be performed at one single calibration pump speed for each pump, in which case the pumps are assumed to be of linear character and only one data point per pump is needed in step b). If there is reason to suspect that the pumps are non-linear, step a) can be performed with a range of calibration pump speeds for each pump and registering the flow rate for each pump speed in the range. The calibration functions can then be calculated in step b) using nonlinear regression or any other suitable curve-fitting method. For complex cases where the flow rate can be expected to vary with back pressure, fluid viscosity, temperature etc., it is also possible to also vary one or more of these variables in step a) and then in step b) use some form of multivariate analysis to calculate the pump calibration functions as multivariate response surfaces. The calibration functions can also be combined into a single calibration function that describes the flow rate ratios between the pumps at given pump speed ratios. In step a), the calibration pump speed can be predetermined and the flow rate just registered from the flow meter. Alternatively, the system may comprise a feedback loop from the flow meter, in which case the calibration pump speed can be varied to provide a predetermined flow rate.

In certain embodiments, the receptacle 2 and 22 is a chromatography column. The mixture of operation fluids can then be used for washing, elution or regeneration of the column. In particular when the mixture is used for elution, the demands for accurate composition of the mixture are high, as the selectivity of a chromatographic separation depends strongly on the composition of the elution fluid. To improve the selectivity and efficiency of the separation, the column can be eluted with a gradient, where the pump speeds are varied to form the gradient in the ratio of the operation fluids in the mixture. The gradient may be a continuous gradient, linear or non-linear with respect to time or total conveyed fluid volume or it can be designed as a series of step gradients. The gradient can be produced from two fluids, such as two buffers, but more complex gradients may also be provided from three or more fluids, in which case three or more pumps will be required.

In some embodiments each calibration fluid volume comprises an operation fluid. An advantage of this is that the system is not contaminated with any extra calibration fluids. Suitably, each pump is calibrated with a fluid to be used in that pump during operation. In the case of gradient elution chromatography, it can be advantageous to first calibrate with the B fluid (the fluid with increasing concentration in the gradient) and then with the A fluid (the fluid with decreasing concentration in the gradient). This means that the tubing will be filled with A fluid at the start of the gradient and no extra washing operation needs to be performed.

In one embodiment a system of valves 8 and 28 (as depicted in FIG. 2) is controlled to disconnect the receptacle 2 and 22 from the pumps 3, 4, 23 and 24 before the calibration in steps a) and c). Then, after the calibration but before the operation in step c), the system of valves 8 and 28 is controlled to connect the receptacle 2 and 22 with the pumps 3, 4, 23 and 24. In other words, the receptacle is by-passed during the pump calibration. This has the advantage that no calibration fluid reaches the receptacle.

Further, shown in FIG. 2, the disposable fluid processing system 20 comprises at least one pressure sensor 27 and at least one throttle valve 29. In this case, step a) can further comprise simulating the back pressure of the receptacle 22 with the throttle valve 29 while registering the flow rates. The throttle valve 29 can e.g. be a pinch valve, which can be applied to disposable tubing without contacting the wetted surfaces. The throttle valve 29 can then be arranged in a feedback loop with the pressure sensor 27 to constrict the flow to the level where the pressure sensor 27 indicates a predetermined back pressure. An advantage of simulating the back pressure of the receptacle is that more accurate pump calibration functions can be calculated for cases where the pump flow rate varies with back pressure. This is particularly advantageous for receptacles that produce significant back pressures, such as chromatography columns and filters, e.g. dead-end filters.

According to one embodiment one of the operation fluids comprises a buffer concentrate and another operation fluid is water or a buffer of lower concentration than the operation fluid comprising a buffer concentrate. This is advantageous for in-line dilution of buffer concentrates, where the diluted buffer is to be used at a later stage in a process. The diluted buffer can be conveyed directly to the point of use, e.g. a chromatography column, a filter setup, bioreactor (optionally via a filter for sterile filtering) etc., but it can also be conveyed to a bag or other storage vessel for intermediate storage, optionally via a filter for sterile filtering or for general particle removal. The buffer concentrate may be a concentrated medium for cell culture. The buffer of lower concentration than the operation fluid comprising a buffer concentrate can have a lower conductivity or ionic strength than said operation fluid, but it can also have a lower concentration of some specific species, e.g. a solvent, detergent or some other additive. More than two operation fluids, such as three or four operation fluids may be mixed according to the invention, in which case more than two pumps may be required.

Referring to FIGS. 1 and 2, in certain embodiments the pumps 3, 4, 23 and 24 are peristaltic pumps. Peristaltic pumps are frequently used in disposable bioprocessing, since the only wetted surface is the elastic tubing used and there is no need for special disposable pump heads. However, they are prone to drift with time, as the position of the tubing will shift during operation due to the mechanical forces. Further, the pump flow versus pressure curve depends strongly on how much the tubing is compressed by the rollers during operation. Compression corresponding to complete closure of the tubing can give an essentially linear curve, while partial closure gives a non-linear curve, particularly at higher back pressures. The compression depends both on the settings of the rollers and on the dimensions and mechanical properties of the particular tubing used. In one embodiment the pumps 3, 4, 23 and 24 are of linear character. If the pumps are non-linear it is particularly advantageous to simulate the back pressure with a throttle valve 29 as described above and to calculate the pump calibration functions for different back pressures.

According to certain embodiments all wetted parts of the disposable fluid processing system 1 and 20 are disposable. The wetted parts can include the tubing, connectors, the flow meter 5 and 25, the pressure sensor 27, the receptacle 2 and 22, and any other vessels used in the system, such as the source(s) of fluid 10, 11, 30 and 31. If other valves than pinch valves are used, the valves 8 and 28 may also be disposable and if non-peristaltic pumps are used, the pump heads may be disposable. In one embodiment all wetted parts of the disposable fluid processing system are sterilized. The sterilization can be performed e.g. by autoclaving, irradiation or treatment with chemicals such as ethylene oxide. It is possible to supply a preassembled package comprising tubing, connectors, the flow meter and the pressure sensor, so that the user just mounts the package into the pumps and valves and connects the system to fluid sources and the receptacle. This preassembled package can advantageously be supplied sterilized. A system where all wetted surfaces are sterilized is required in any application involving cell culture, extracorporal treatment of body fluids etc., but sterility is also an advantage in other applications, e.g. where the final product is a biopharmaceutical to be administered parenterally.

In one aspect illustrated by FIGS. 1-3, the present invention discloses a disposable fluid processing system 1 and 20 which comprises at least one flow meter 5 and 25, at least one receptacle 2 and 22, at least one control unit 6 and 26 (as depicted in FIG. 2) and at least two pumps 3, 4, 23 and 24, each pump connected to at least one source of fluid 10, 11, 30 and 31, wherein a. the pumps 3, 4, 23 and 24 are coupled to the flow meter 5 and 25 and the receptacle by tubing and a system of valves 8 and 28 adapted to provide fluid connection between either one or both of the pumps 3, 4, 23 and 24 and the flow meter 5 and 25 or both pumps 3, 4, 23 and 24 in parallel and the receptacle 2 and 22, b. the control unit 6 and 26 is electrically connected to and adapted to control the pumps 3, 4, 23 and 24 and the system of valves 8 and 28 and the control unit 6 and 26 is electrically connected to and adapted to receive data output from the flow meter 5 and 25, c. the control unit 6 and 26 is adapted to for each pump 3, 4, 23 and 24 pump a calibration fluid volume through the pump to, from or via the flow meter 5 and 25 at one or more calibration pump speeds registering the flow rate using data output from the flow meter 5 and 25 and for each pump calculate a pump calibration function from the calibration pump speed and the flow rate and d. the control unit 6 and 26 is adapted to control the pumps 3, 4, 23 and 24 for mixing two or more operation fluids to a predetermined mixture ratio and predetermined flow rate by controlling the pump speed of the respective pumps 3, 4, 23 and 24 in accordance with the pump calibration functions.

The system of valves 8 and 28 can comprise pinch valves mounted on the tubing, but it can also comprise three- or four-way valves mounted at tubing junctions. The control unit 6 and 26 can comprise a computer, a programmable logic controller or any other type of process controller.

The control unit 6 and 26 can be adapted to provide feedback loops from the flow meter 5 ad 25 to each pump 3, 4, 23 and 24. These feedback loops can be used during calibration of the pumps to make each pump deliver a predetermined flow rate and recording the corresponding calibration pump speed.

The receptacle 2 and 22 can be a chromatography column, but also a filter, a storage vessel like e.g. a bag or it can be a bioreactor for e.g. cell culture. According to an embodiment illustrated by FIG. 2, the disposable fluid processing system can further comprise at least one pressure sensor 27 and at least one throttle valve 29, wherein said throttle valve 29 is arranged in a feedback loop with said pressure sensor 27 to simulate the back pressure of the receptacle 22.

In one embodiment the disposable fluid processing system is arranged for in-line dilution of a buffer concentrate, wherein a first operation fluid comprises the buffer concentrate and a second operation fluid is water or a buffer of lower concentration or conductivity than the first operation fluid. In a specific embodiment the first operation fluid comprises a concentrated medium for cell culture.

In one embodiment the pumps 3, 4, 23 and 24 are peristaltic pumps. The pumps 3, 4, 23 and 24 can also be of linear character, which facilitates the calibration procedure.

According to one embodiment, the flow meter 5 and 25 can be an in-line flow meter, i.e. where the fluids pass through a channel and the fluid velocity is measured by e.g. ultrasound, pressure drop, a turbine, Coriolis forces, optical effects, magnetic effects etc. In a specific embodiment the flow meter is an ultrasound flow meter. Alternatively, the flow meter can be off-line, e.g. by diverting the fluid to a bag or other vessel and measuring the weight increase or by pumping fluid from a bag etc. and measuring the weight decrease. The flow meter 5 and 25 can be placed anywhere in the system where it can be connected to each pump, either before or after the pumps 3, 4, 23 and 24.

In one embodiment all wetted parts of the disposable fluid processing system are disposable and/or sterilized.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for conveying a mixture of at least two operation fluids to a receptacle in a disposable fluid processing system comprising a single flow meter, a first pump and a second pump, each pump being connected to at least one source of fluid, at least one pressure sensor and at least one throttle valve, said method comprising:
   a) if the first pump and the second pump are linear, then pumping a first calibration fluid volume through the first pump and a second calibration fluid volume through the second pump via the single flow meter at a same calibration pump speed for the first pump and the second pump and registering a flow rate using data output from the single flow meter to calibrate the first pump and the second pump in relation to each other, wherein the first calibration fluid volume comprises one operation fluid of the at least two operation fluids and the second calibration fluid volume comprise the other operation fluid of the at least two operation fluids wherein the at least two operation fluids are different from each other, and if the first pump and the second pump are non-linear, then pumping the first calibration fluid volume and the second calibration fluid volume at a same range of a plurality of calibration pump speeds for the first pump and the second pump, and registering the flow rate using the data output from the single flow meter for each calibration pump speed in the range using data output from the single flow meter:
   b) simulating a back pressure within a flow to said receptacle with said throttle valve while registering the flow rate for the first pump and the second pump, wherein an input of said pressure sensor is downstream from the first pump and the second pump and connected to an output of the first pump and an output of the second pump via a first valve of a system of valves; and wherein an output of said pressure sensor is connected to an input of the throttle valve downstream from said pressure sensor and an output of the throttle valve is connected to the receptacle downstream from the throttle valve via a second valve of a system of valves forming a feedback loop therebetween to constrict the flow to a level where the pressure sensor indicates a predetermined back pressure;

c) calculating a pump calibration function for the first pump and for the second pump upon indication of the predetermined back pressure of the receptacle, the pump calibration function being a mathematical relationship between said same calibration pump speed and said flow rate; and d) mixing the at least two operation fluids to a predetermined mixture ratio and predetermined flow rate by controlling the pump speed of the first pump and the second pump in accordance with said pump calibration functions.

2. The method of claim 1, wherein before step a) the system of valves is controlled to disconnect said receptacle from the first pump and the second pump and before step d) said system of valves is controlled to connect said receptacle with the first pump and the second pump.

3. The method of claim 1, wherein said receptacle is a chromatography column.

4. The method of claim 3, wherein in step d) said pump speeds are varied so as to form a gradient in the predetermined mixture ratio of the at least two operation fluids mixed.

5. The method of claim 3, further comprising a step e] eluting said chromatography column with the at least two operation fluids mixed.

6. The method of claim 1, wherein one operation fluid of the at least two operation fluids comprises a buffer concentrate and another operation fluid of the at least two operation fluids is water or a buffer of a concentration different from a concentration of the operation fluid comprising the buffer concentrate.

7. The method of claim 1, wherein the first pump and the second pump are peristaltic pumps.

8. The method of claim 1, wherein all wetted parts of said disposable fluid processing system are disposable.

9. The method of claim 1, wherein all wetted parts of said disposable fluid processing system are sterilized.

10. The method of claim 1, wherein if the first pump and the second pump are non-linear, the throttle valve is arranged to simulate the back pressure in order to calculate the pump calibration functions for different back pressures.

* * * * *